(12) United States Patent
Goldman et al.

(10) Patent No.: US 12,264,153 B2
(45) Date of Patent: Apr. 1, 2025

(54) PHEBOX LIGANDS AND METHODS OF MAKING SAME

(71) Applicant: RUTGERS, THE STATE UNIVERSITY OF NEW JERSEY, New Brunswick, NJ (US)

(72) Inventors: Alan S. Goldman, Piscataway, NJ (US); Thomas R. Dugan, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 18/641,842

(22) Filed: Apr. 22, 2024

(65) Prior Publication Data

US 2024/0279211 A1  Aug. 22, 2024

Related U.S. Application Data

(60) Division of application No. 17/939,047, filed on Sep. 7, 2022, now Pat. No. 11,993,592, which is a continuation of application No. 17/209,850, filed on Mar. 23, 2021, now Pat. No. 11,465,996.

(60) Provisional application No. 62/993,154, filed on Mar. 23, 2020.

(51) Int. Cl.
    *C07D 413/10* (2006.01)
(52) U.S. Cl.
    CPC .................. *C07D 413/10* (2013.01)
(58) Field of Classification Search
    CPC .................................................. C07D 413/10
    USPC ........................................................ 548/237
    See application file for complete search history.

(56) References Cited

U.S. PATENT DOCUMENTS

| | | |
|---|---|---|
| 11,020,731 B2 | 6/2021 | Goldman et al. |
| 11,465,996 B2 | 10/2022 | Goldman et al. |
| 2013/0317212 A1 | 11/2013 | Nazeeruddin et al. |
| 2023/0022558 A1 | 1/2023 | Goldman et al. |

FOREIGN PATENT DOCUMENTS

WO  2013130972 A1  9/2013

OTHER PUBLICATIONS

Adams, et al., "Investigation of CF3 Iridium PCP Pincer Catalytic Dehydrogenation and Decarbonylation Chemistry", Organometallics, vol. 31, No. 4, 2012, pp. 1439-1447.
Allen, et al., "Regeneration of an Iridium(III) Complex Active for Alkane Dehydrogenation Using Molecular Oxygen", Organometallics, vol. 33, 2014, pp. 1337-1340.
Gao, et al., "Iridium-catalyzed dehydrogenative coupling of ethylene to form 1,3-butadiene", Rutgers University 2017 Central Regional Meeting (CERM) presentation. Jun. 8, 2017.
Gao, et al., "ß-Hydride Elimination and C-H Activation by an Iridium Acetate Complex, Catalyzed by Lewis Acids. Alkane Dehydrogenation Cocatalyzed by Lewis Acids and [2,6-Bis(4,4-dimethyloxazolinyl)-3,5-dimethylphenyl] iridium", J. Am. Chem. Soc. 2017, 139, 6338-6350.
Ito, et al., "Efficient Preparation of New Rhodium- and Iridium-[Bis(oxazo-linyl)-3,5-dimethylphenyl] Complexes by C-H Bond Activation: Applications in Asymmetric Synthesis", Adv. Synth. Catal. 2006, 348, 1235-1240.
Ito, et al., "Intermolecular C-H Bond Activation of Alkanes and Arenes by NCN Pincer Iridium(III) Acetate Complexes Containing Bis(oxazolinyl)phenyl Ligands", Organometallics, vol. 31, 2012, pp. 4442-4449.
Motoyama, et al., "Bis(oxazolinyl)phenylrhodium(III) Aqua Complexes: Synthesis, Structure, Enantioselective Allylation of Aldehydes, and Mechanistic Studies", Organometallics, vol. 28, No. 8, Mar. 22, 2001, pp. 1580-1591.
Motoyama, et al., "Chiral bis(oxazolinyl)phenylrhodium(III) complexes as Lewis acid catalysts for enantioselective allylation of aldehydes", Chem Comm (Cambridge), Issue 2, 1999, pp. 131-132.
Motoyama, et al., "Novel Asymmetric Michael Addition of alpha-Cyanopropionates to Acrolein by the Use of a Bis(oxazolinyl)phenylstannane-Derived Rhodium(III) Complex as a Chiral Lewis Acid Catalyst", Chem Eur J, vol. 8, No. 13, Jun. 24, 2002, pp. 2968-2975.
Motoyama, et al., "Synthesis and X-ray Crystal Structures of Bis(oxazolinyl)phenyl-Derived Chiral Palladium(II) and Platinum(II) and -(IV) Complexes and Their Use in the Catalytic Asymmetric Aldol-Type Condensation of Isocyanides and Aldehydes", Organometallics, vol. 21, No. 16, Jul. 3, 2002, pp. 3408-3416.
Nishiyama, et al., "High Performance of Rh(Phebox) Catalysts in Asymmetric Reductive Aldol Reaction: High Anti-Selectivity", J Am Chem Soc, vol. 127, No. 19, Apr. 26, 2005, pp. 6972-6973.
Nishiyama, H., "Synthesis and use of bisoxazolinyl-phenyl pincers", Chem Soc Rev, vol. 36, No. 7, Jul. 2007, pp. 1133-1141.
Nobbs, et al., "Thio-Pybox and Thio-Phebox complexes of chromium, iron, cobalt and nickel and their application in ethylene and butadiene polymerisation catalysis.", Dalton Trans., 2012, 41, 5949-5964.
Nückel, et al., "Transition Metal Complexes with Sterically Demanding Ligands, 3.1 Synthetic Access to Square-Planar Terdentate Pyridine-Diimine Rhodium(I) and Iridium(I) Methyl Complexes: Successful Detour via Reactive Triflate and Methoxide Complexes(I)", Organometallics, vol. 20, 2001, pp. 4345-4359.
Ohshima, et al., "C1-Symmetric Rh/Phebox-Catalyzed Asymmetric Alkynylation of alpha-Ketoesters", Angew Chem Int Ed, vol. 50, 2011, pp. 6296-6300.
Pahls, et al., "Understanding the Effect of Ancillary Ligands on Concerted Metalation-Deprotonation by (dmPhebox) Ir(OAc)2(H2O) Complexes: A DFT Study", Organometallics, vol. 33, 2014, pp. 6413-6419.

(Continued)

*Primary Examiner* — Kahsay Habte
(74) *Attorney, Agent, or Firm* — Saul Ewing LLP; Domingos J. Silva; Kathryn Doyle

(57) ABSTRACT

The present disclosure provides compounds which are useful for a number of catalytic transformations of organic molecules, non-limiting examples including dehydrogenation of alkanes. The present disclosure further relates to methods of preparing the compounds of the present disclosure.

9 Claims, 1 Drawing Sheet

(56) References Cited

OTHER PUBLICATIONS

Takemoto, et al., "Highly efficient Suzuki-Miyaura coupling reactions catalyzed by bis(oxazolinyl)henyl-Pd(II) complex", Tetrahedron Lett, vol. 48, No. 19, May 7, 2007, pp. 3397-3401.

Yuan, et al., "Effect of Carboxylate Ligands on Alkane Dehydrogenation with (dmPhebox)Ir Complexes", ACS Catal, vol. 8, 2018, pp. 2326-2329.

Zhou, "Computational Study of Pincer Iridium Catalytic Systems: C-H, N-H, and C-C Bond Activation and C-C Coupling Reactions.", A dissertation submitted to the Graduate School-New Brunswick Rutgers, The State University of New Jersey, May 2017.

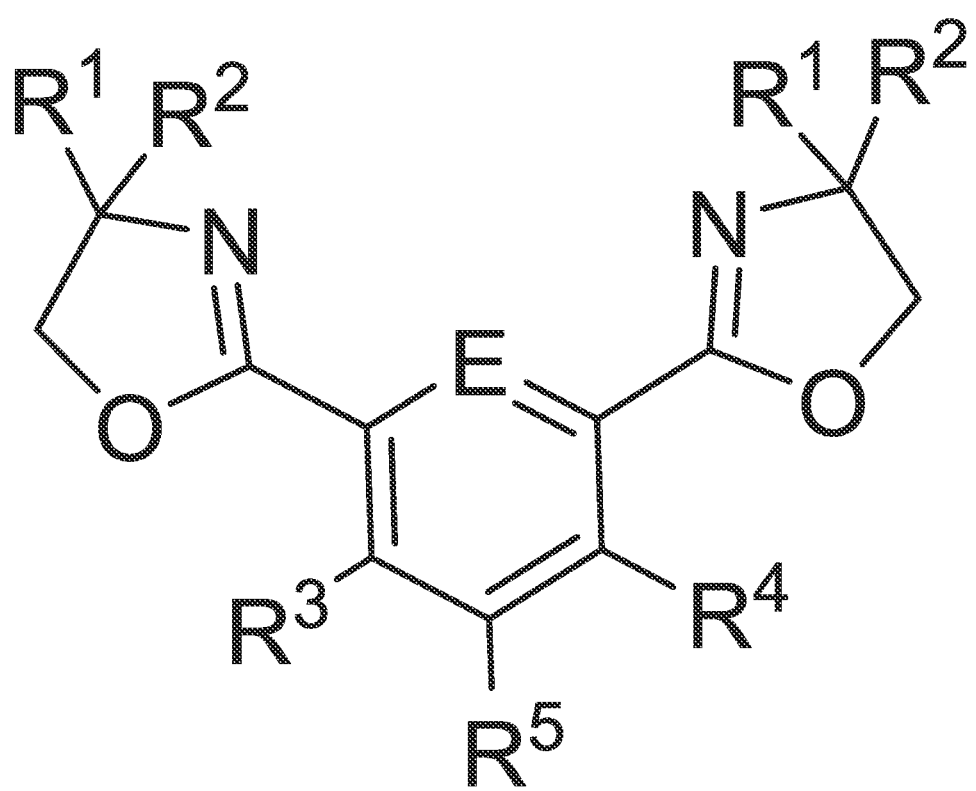
Formula (I)

PHEBOX LIGANDS AND METHODS OF MAKING SAME

CROSS-REFERENCE TO RELATED APPLICATIONS

This application is a divisional of, and claims priority under 35 U.S.C. § 121 to, U.S. application Ser. No. 17/939,047, filed Sep. 7, 2022, now allowed, which is a continuation of, and claims priority to, U.S. application Ser. No. 17/209,850, filed Mar. 23, 2021, now issued as U.S. Pat. No. 11,465,996, which claims priority under 35 U.S.C. § 119(e) to U.S. Provisional Patent Application No. 62/993,154, filed Mar. 23, 2020, the contents of which are incorporated by reference herein in their entireties.

BACKGROUND

Phebox ligands are useful for developing metal complexes that catalyze a wide variety of chemical reactions. These reactions include, for example, conversion of low-value alkanes to high-value alkenes, or conversion of alkanes to other high-value unsaturated products such as aldehydes and alcohols. Other examples of the reactions that are catalyzed by phebox based metal complexes are—Suzuki-Miyaura coupling reactions of aryl boronic acids and their derivatives with aryl halides to give the corresponding biaryl products, enantioselective allylation of aldehydes, asymmetric Michael addition of α-cyanopropionates to acrolein, asymmetric reductive aldol reaction of aldehydes and α,β-unsaturated esters with hydrosilanes to give the corresponding β-hydroxypropionates, and asymmetric alkynylation of α-ketoester with various aryl and alkyl substituted terminal alkynes to provide the corresponding chiral tertiary propargylic alcohols.

However, despite their use in wide variety of reactions, there is still an unmet need in the art to develop phebox ligands, which can be complexed with metals to yield stable, convenient to synthesize, and highly effective catalysts. The present disclosure addresses this unmet need.

BRIEF SUMMARY OF THE INVENTION

The present disclosure provides, in part, certain compounds of formula (I), or a salt or solvate thereof:

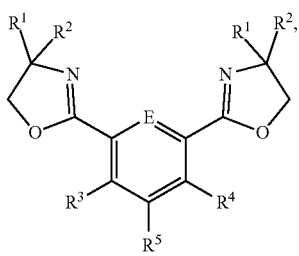

(I)

wherein the various substituents in the compounds of formula (I) are defined elsewhere herein. In one aspect, the compounds of the present disclosure are useful for a number of catalytic transformations of organic molecules, including transformations of alkanes generally requiring harsh conditions (e.g. dehydrogenation). The present disclosure further relates to methods of preparing compounds of formula (I).

BRIEF DESCRIPTION OF THE FIGURES

The drawings illustrate generally, by way of example, but not by way of limitation, various embodiments of the present application.

FIG. 1 shows the structure of the compound of Formula (I), in accordance with various embodiments.

DETAILED DESCRIPTION OF THE INVENTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

Definitions

The term "about" as used herein can allow for a degree of variability in a value or range, for example, within 10%, within 5%, or within 1% of a stated value or of a stated limit of a range, and includes the exact stated value or range.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to vinyl, —CH=C=CCH$_2$, —CH—CH(CH$_3$), —CH=C(CH$_3$)$_2$, —C(CH$_3$)=CH$_2$, —C(CH$_3$)—CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C=CH, —C=C(CH$_3$), —C=C(CH$_2$CH$_3$), —CH$_2$C=CH, —CH$_2$C=C(CH$_3$), and —CH$_2$C=C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The term "atm" as used herein refers to a pressure in atmospheres under standard conditions. Thus, 1 atm is a pressure of 101 kPa, 2 atm is a pressure of 202 kPa, and so on.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "deamination" as used herein refers to one or more organic reactions whereby a C—N moiety present in an organic compound is converted to a C—H moiety. In certain embodiments, the C—N moiety is a primary amine. In certain embodiments, the primary amine is converted to a diazonium species.

The term "diazotization" as used herein refers to an organic reaction whereby a primary amine (R—NH$_2$) is converted to a diazonium species (R—N$_2^+$). In certain embodiments, the primary amine is reacted with a nitrite species, non-limiting examples including t-BuONO and NaNO$_2$.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a C$_2$-heteroaryl can be a 5-ring with two carbon atoms and three heteroatoms, a 6-ring with two carbon atoms and four heteroatoms and so forth. Likewise a C$_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed herein. Representative substituted heteroaryl groups can be substituted one or more times with groups such as those listed herein.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

The term "heterocyclyl" as used herein refers to aromatic and non-aromatic ring compounds containing three or more ring members, of which one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a C$_2$-heterocyclyl can be a 5-ring with two carbon atoms and three heteroatoms, a 6-ring with two carbon atoms and four heteroatoms and so forth. Likewise a C$_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed herein. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed herein.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "hydrocarbon" or "hydrocarbyl" as used herein refers to a molecule or functional group that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$hydrocarbyl means the hydrocarbyl group can be methyl ($C_1$), ethyl ($C_2$), propyl ($C_3$), or butyl ($C_4$), and $(C_0-C_b)$hydrocarbyl means in certain embodiments there is no hydrocarbyl group.

The term "independently selected from" as used herein refers to referenced groups being the same, different, or a mixture thereof, unless the context clearly indicates otherwise. Thus, under this definition, the phrase "$X^1$, $X^2$, and $X^3$ are independently selected from noble gases" would include the scenario where, for example, $X^1$, $X^2$, and $X^3$ are all the same, where $X^1$, $X^2$, and $X^3$ are all different, where $X^1$ and $X^2$ are the same but $X^3$ is different, and other analogous permutations.

The term "in situ" as used herein refers to the generation of a chemical entity for use in one or more chemical reactions without purification of the chemical species (i.e. in the reaction mixture).

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted $(C_1-C_{100})$hydrocarbyl, wherein R can be hydrogen (in examples that include other carbon atoms) or a carbon-based moiety, and wherein the carbon-based moiety can be substituted or unsubstituted.

The term "room temperature" as used herein refers to a temperature of about 15° C. to 28° C.

The term "solvent" as used herein refers to a liquid that can dissolve a solid, liquid, or gas. Non-limiting examples of solvents are silicones, organic compounds, water, alcohols, ionic liquids, and supercritical fluids.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, $(C_1-C_{100})$hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

Compounds

Phebox ligands are useful for a number of catalytic transformations of organic molecules, including transformations of alkanes generally requiring harsh conditions. Since catalytic transformations using this class of ligands intrinsically involve the activation of C—H bonds, the degradation of the phebox ligand via reactions of the C—H bonds of the aryl position (benzylic or aryl C—H bonds) is potentially problematic. It is therefore sought herein to protect these positions with specific groups, such as but not limited to —CF$_3$ groups.

In one aspect, a compound of formula (I), or a salt or solvate thereof, is:

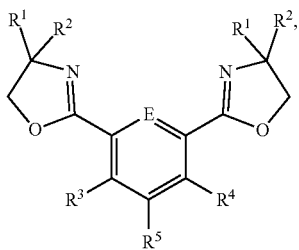
(I)

wherein:
- R$^1$ and R$^2$ are each CH$_3$, or R$^1$ and R$^2$ taken together are —(CH$_2$)$_4$— or —(CH$_2$)$_5$—;
- R$^3$ is selected from the group consisting of CF$_3$, CF$_2$CF$_3$, CN, and NO$_2$;
- R$^4$ is selected from the group consisting of CF$_3$, CF$_2$CF$_3$, CN, and NO$_2$;
- R$^5$ is selected from the group consisting of H, CF$_3$, CF$_2$CF$_3$, CN, and NO$_2$; and
- E is CH or N.

In certain embodiments, R$^1$ and R$^2$ are each CH$_3$.
In certain embodiments, R$^3$ and R$^4$ are each CF$_3$.
In certain embodiments, E is CH.
In certain embodiments, the compound of formula (I) is selected from the group consisting of

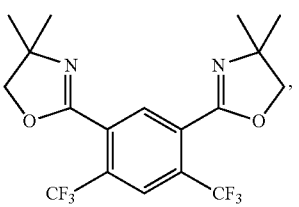 [SMILES: CC1(C)COC(c2cc(C3=NC(C)(C)CO3)c(C(F)(F)F)cc2C(F)(F)F)=N1]
(Ia)

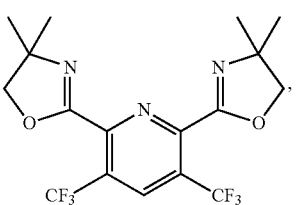
(Ib)

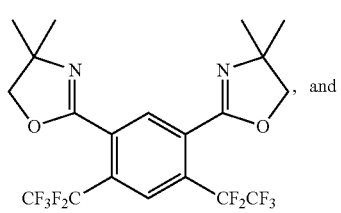
(Ic)

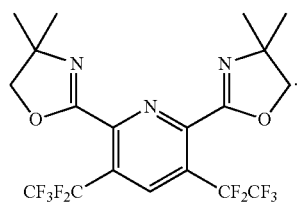
(Id)

In certain embodiments, the compound of formula (I) is selected from the group consisting of

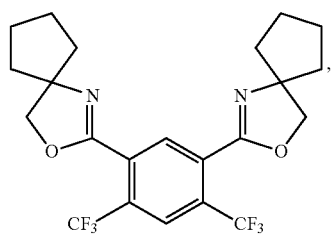
(Ie)

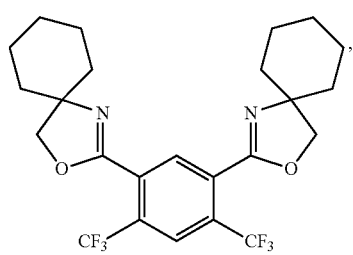
(If)

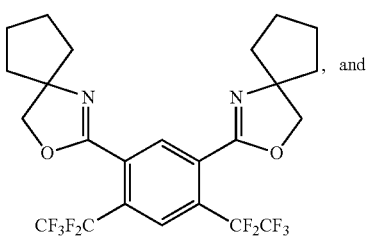
(Ig)

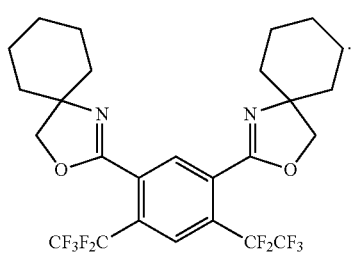
(Ih)

The compounds described herein can possess one or more stereocenters, and each stereocenter can exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In certain embodiments, the compound(s) described herein can exist as tautomers. All tautomers are included within the scope of the compounds presented herein.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Methods of Making Compounds of Formula (I)

In another aspect, a method of making the compound of formula (I) is provided. The method comprises:
converting

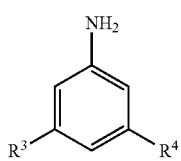
(II)

into

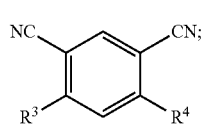
(V)

and
contacting

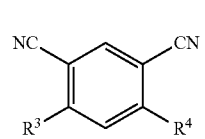
(V)

with

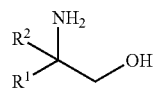
(VI)

to provide the compound of formula (I).

In certain embodiments, converting compounds of formula (II) to compounds of formula (V) comprises:
brominating

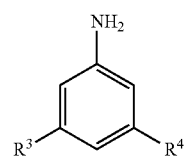
(II)

to provide

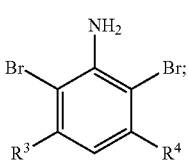
(III)

deaminating

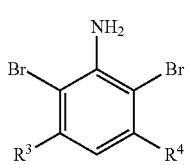
(III)

to provide

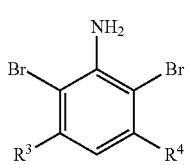
(IV)

cyanating

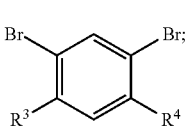
(IV)

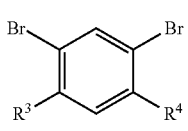
(IV)

to provide

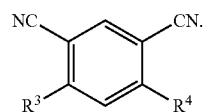

In certain embodiments, brominating comprises contacting FeBr$_3$ with the compound of formula (II). In certain embodiment, the compound of formula (II) is 3,5-bis(trifluoromethyl)aniline having formula

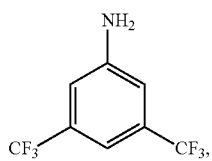

and the bromination can be performed as shown in Scheme 1.

Scheme 1

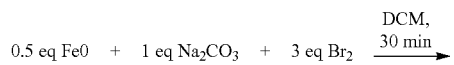

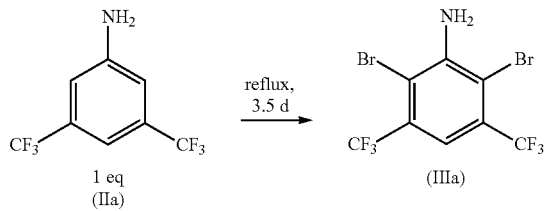

In certain embodiments, FeBr$_3$ can be generated in situ before addition of the aniline to the reaction system. The reaction is scalable and can be performed up to, for example, 30 mmol scale in at least about 90% yield or higher to obtain 2,6-dibromo-3,5-bis(trifluoromethyl)aniline (IIIa). In various embodiments, the compound of formula (II) contacts the FeBr$_3$ after the generation of FeBr$_3$ is completed.

In certain embodiments, the purification of (IIIa) is performed using flash column chromatography.

In certain embodiments, the deamination of compound of formula (III) occurs via diazotization and warming. In certain embodiments, warming can include letting the reaction come up to room temperature on its own.

In certain embodiments, the compound of formula (III) is 2,6-dibromo-3,5-bis(trifluoromethyl)aniline having formula (IIIa), and the deamination can be performed as shown in Scheme 2.

Scheme 2

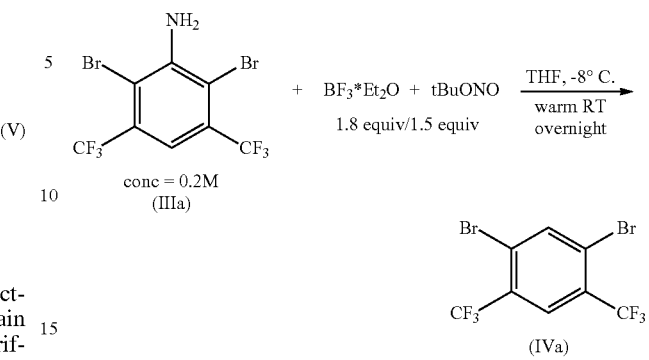

Deamination of (IIIa) is performed using a diazonium salt formation procedure. Under the reaction conditions used, in certain embodiments the deaminated product-1,5-dibromo-2,4-bis(trifluoromethyl)benzene having formula (IVa) is isolated, suggesting that the desired diazomium salt is fairly unstable under the reaction conditions. Without wishing to be limited by any theory, this reaction may occur through a radical mechanism that results in formation of the deaminated product. The deamination reaction is easily scalable.

In certain embodiments, cyanating of the compound of formula (IV) comprises contacting the compound of formula (IV) with a transition metal cyanide.

In certain embodiments, the compound of formula (IV) is 1,5-dibromo-2,4-bis(trifluoromethyl)benzene, having formula (IVa), the transition metal cyanide is CuCN, and the cyanation reaction is performed as shown in Scheme 3 to obtain 1,5-bis(cyano)-2,4-bis(trifluoromethyl)benzene, having formula (Va).

Scheme 3

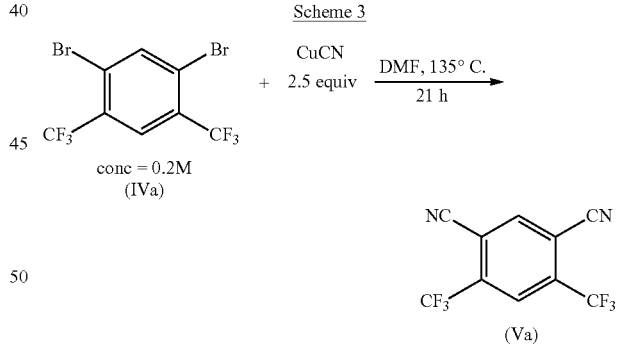

The cyanation product can be obtained by purification of the reaction mixture by column chromatography, for example.

In certain embodiments, the compound of formula (V) is contacted with the compound of formula (VI) in the presence of a Lewis acid to obtain the Phebox ligand. In certain embodiments, the Lewis acid is Zn(OTf)$_2$.

In certain embodiments, the compound of formula (V) is 1,5-bis(cyano)-2,4-bis(trifluoromethyl)benzene, having formula (Va), and it is reacted with 2-amino-3-hydroxy-2-methyl-propane (VIa) under Witte-Seeliger conditions to yield a bis-CF$_3$-Phebox ligand (VIIa) (Scheme 4).

Scheme 4

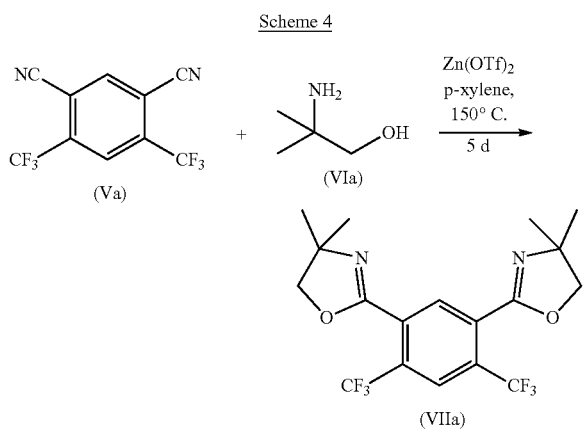

(VIIa)

In certain embodiments, the Witte-Seeliger reaction is performed in a sealed flask over the period of about 2, 3, 4, or about 5 d.

Compounds described herein are synthesized using any suitable procedures starting from compounds that are available from commercial sources, or are prepared using procedures described herein.

EXAMPLES

The disclosure further describes additional details by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples therefore, specifically point out the preferred embodiments of the disclosure, and are not to be construed as limiting in any way the remainder of the disclosure.

Example 1: Synthesis of Phebox Ligand

Synthesis of Compound (IIIa)-2,6-dibromo-3,5-bis(trifluoromethyl)aniline

Iron powder (280 mg, 5.01 mmol, 0.5 equiv), sodium carbonate (1.075 g, 10.14 mmol, 1 equiv), and dichloromethane (50 mL) were added to a round bottomed flask equipped with a stir bar. Bromine (1.55 mL, 30.1 mmol, 3 equiv) was added to the mixture via syringe to give a dark red mixture which was stirred for 30 min. 3,5-bis(trifluoromethyl)aniline (1.57 mL, 10.0 mmol, 1 equiv) was added via syringe. The flask was equipped with a reflux condenser, and the dark red mixture was heated to reflux. The reaction was monitored by TLC in 10% EtOAc/hexanes (v:v) where the Rf of the product is 0.4. After 3.5 d, the dark red mixture was cooled to room temperature and was treated with saturated sodium carbonate (200 mL) to give an orange biphasic mixture. The organic layer was separated in a separatory funnel, and the aqueous layer was extracted with DCM (3×30 mL) and Et$_2$O (2×30 mL). The organic extracts were dried with MgSO$_4$ and were filtered through glasswool to give a light orange solution. The volatile components were removed under educed pressure to give a light orange residue. The product was purified by flash column chromatography using 250 g of silica gel and 10% EtOAc/hexanes (v:v). The product fractions were combined and the volatile components were removed under reduced pressure to give the product as a semi-crystalline off-white solid (3.74 g, 96.8% yield). $^1$H NMR (400 MHZ, CDCl$_3$): δ 7.37 (s, 1H), 5.24 (s, 2H) ppm. $^{13}$C{$^1$H} NMR (100 MHZ, CDCl$_3$): δ 109.5, 114.3 (m, $J_{CF}$=6 Hz), 121.1 (q, $J_{CF}$=272 Hz), 130.1 (q, $J_{CF}$=32 Hz), 145.5 ppm. $^{19}$F{$^1$H} NMR (282.2 MHz, CDCl$_3$): δ −63.5 (s) ppm.

Synthesis of Compound (IVa)-1,5-dibromo-2,4-bis(trifluoromethyl)benzene

Schlenk techniques under Ar were used for this procedure. 2,6-dibromo-3,5-bis(trifluoromethyl)aniline (2.902 g, 7.5 mmol) was added to a Schlenk flask along with dry THF (33 mL). The colorless solution was cooled to −8° C. (T was maintained between −6° C. and −8° C.) in an ice bath. BF$_3$ etherate (1.7 mL, 13.7 mmol) was added via syringe and no change was observed. After 5 min, tert-butyl nitrite (1.4 mL, 11.8 mmol) was added to the solution via syringe and no change was observed. After 1 h, a bright yellow solution was observed and T=−6° C. The solution was allowed to slowly warm overnight in the ice bath. After 19 h, a bright orange solution was observed and T=17 C. TLC (10% EtOAc/hexanes) was performed and no starting material was observed. The volatile components were removed by evaporation aided by compressed air to give an oily red-brown residue. The residue was purified via column chromatography using 125 g of silica gel, 10% EtOAc/hexanes, and 25 mL fractions. The product fractions were combined and the volatile components were removed by evaporation aided by compressed air. The off-white solid was then dried under high vacuum to give 1.530 g of product (54.9% yield). 1H NMR (500 MHZ, CDCl$_3$): δ 8.12 (s, 1H), 7.95 (s, 1H) ppm. $^{13}$C{$^1$H} NMR (125 MHZ, CDCl$_3$): δ 123.3 (q, $J_{CF}$=272.5 Hz), 124.9 (m, $J_{CF}$=1 Hz), 126.9 (sep, $J_{CF}$=5 Hz), 130.1 (q, $J_{CF}$=32.5 Hz), 141.02 ppm. $^{19}$F{$^1$H} NMR (470.4 MHZ, CDCl$_3$): δ −63.40 (s) ppm.

Synthesis of Compound (Va)-1,5-bis(cyano)-2,4-bis(trifluoromethyl)benzene

Schlenk techniques under Ar were used for this procedure. CuCN (230 mg, 2.57 mmol) was added as a solid to a small bomb flask. 1,5-dibromo-2,4-bis(trifluoromethyl)benzene (373 mg, 1.0 mmol) was weighed into a small vial. The organic starting material was transferred quantitatively using dry DMF (5 mL) to the bomb flask. The flask was sealed and the mixture was heated at 150° C. After 21 h, the orange mixture with white precipitate was cooled to room temperature. TLC (20% EtOAc/hexanes) was performed and no starting material was observed. The mixture was transferred to a small Schlenk flask and the volatile components were removed under reduced pressure to give a brown residue. The residue was purified via column chromatography using 20 g of silica gel, 20% EtOAc/hexanes, and 10 mL fractions. The product fractions were combined and the volatile components were removed under reduced pressure to give product as a pale light yellow powder (209 mg, 79.2%). 1H NMR (500 MHZ, CDCl$_3$): δ 8.32 (s, 1H), 8.23 (s, 1H) ppm. $^{13}$C{$^1$H} NMR (125 MHZ, CDCl$_3$): δ 112.39, 115.31, 122.0

(q, $J_{CF}$=273.8 Hz), 125.6 (sep, $J_{CF}$=5 Hz), 137.2 (q, $J_{CF}$=35 Hz), 140.12 ppm. $^{19}F\{^{1}H\}$ NMR (470.4 MHZ, CDCl$_3$): δ −62.82 (s) ppm.

Synthesis of Compound (VIIa)-bis-CF 3-Phebox

Schlenk techniques under Ar were used for this procedure. 1,5-bis(cyano)-2,4-bis(trifluoromethyl)benzene (129 mg, 0.488 mmol) and Zn(OTf)$_2$ (18.4 mg, 0.051 mmol) were added as solids to a small bomb flask. P-xylene (2.5 mL) was added to give a clear mixture. The amino-alcohol (0.10 mL, 1.05 mmol) was added as a liquid via syringe. The flask was sealed and the mixture was heated at 150° C. for 5 d.

Enumerated Embodiments

The following exemplary embodiments are provided, the numbering of which is not to be construed as designating levels of importance:

Embodiment 1 provides a compound of formula (I), or a salt or solvate thereof:

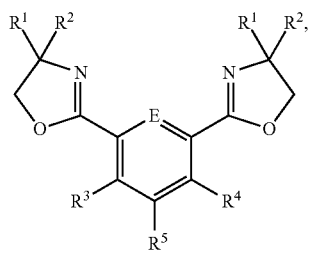
(I)

wherein:
R$^1$ and R$^2$ are each CH$_3$, or R$^1$ and R$^2$ taken together are —(CH$_2$)$_4$— or —(CH$_2$)$_5$—;
R$^3$ is selected from the group consisting of CF$_3$, CF$_2$CF$_3$, CN, and NO$_2$;
R$^4$ is selected from the group consisting of CF$_3$, CF$_2$CF$_3$, CN, and NO$_2$;
R$^5$ is selected from the group consisting of H, CF$_3$, CF$_2$CF$_3$, CN, and NO$_2$; and
E is CH or N.

Embodiment 2 provides the compound of Embodiment 1, wherein R$^1$ and R$^2$ are CH$_3$.

Embodiment 3 provides the compound of any of Embodiments 1-2, wherein R$^3$ and R$^4$ are CF$_3$.

Embodiment 4 provides the compound of any of Embodiments 1-3, wherein E is CH.

Embodiment 5 provides the compound of any of Embodiments 1-4, wherein the compound is

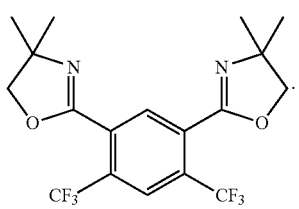

Embodiment 6 provides a method of making the compound of any of Embodiments 1-5, the method comprising:
converting

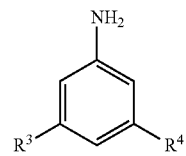
(II)

into

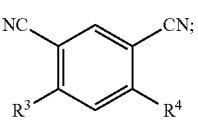
(V)

and
contacting

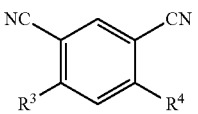
(V)

with

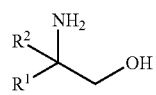
(VI)

to provide the compound of formula (I).

Embodiment 7 provides the method of Embodiment 6, wherein converting (II) to (V) comprises:
brominating

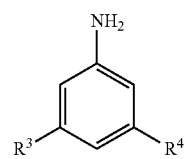
(II)

to provide

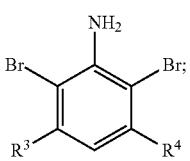
(III)

deaminating

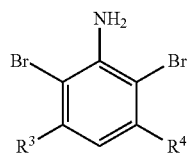

to provide

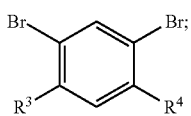

cyanating

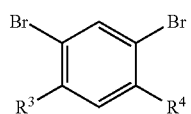

to provide

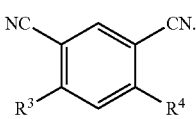

Embodiment 8 provides the method of any of Embodiments 6-7, wherein brominating comprises contacting $FeBr_3$ with the compound of formula (II).

Embodiment 9 provides the method of any of Embodiments 6-8, wherein the $FeBr_3$ is generated in situ.

Embodiment 10 provides the method of any of Embodiments 6-9, wherein the compound of formula (II) contacts the $FeBr_3$ after the $FeBr_3$ is generated.

Embodiment 11 provides the method of any of Embodiments 6-10, wherein the deaminating of compound of formula (III) occurs via diazotization and warming.

Embodiment 12 provides the method of any of Embodiments 6-11, wherein the cyanating of the compound of formula (IV) comprises contacting the compound of formula (IV) with a cyanide salt.

Embodiment 13 provides the method of any of Embodiments 6-12, wherein the cyanide salt is a transition metal cyanide salt.

Embodiment 14 provides the method of any of Embodiments 6-13, wherein the transition metal cyanide salt is CuCN.

Embodiment 15 provides the method of any of Embodiments 6-14, wherein the compound of formula (V) is contacted with the compound of formula (VI) in the presence of a Lewis acid.

Embodiment 16 provides the method of any of Embodiments 6-15, wherein the Lewis acid is $Zn(OTf)_2$.

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this disclosure herein has been presented with reference to specific embodiments, it is apparent that other embodiments and variations of this disclosure may be devised by others skilled in the art without departing from the true spirit and scope of this disclosure. The appended claims are intended to be construed to include all such embodiments and equivalent variations.

What is claimed is:

1. A compound of formula (V), or a solvate thereof:

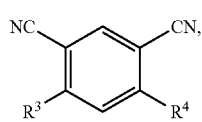

wherein:

$R^3$ is selected from the group consisting of $CF_3$, $CF_2CF_3$, CN, and $NO_2$;

$R^4$ is selected from the group consisting of $CF_3$, $CF_2CF_3$, CN, and $NO_2$; and with the provisos that:

if one of $R^3$ and $R^4$ is CN, then the other is $CF_2CF_3$ or $NO_2$;

if one of $R^3$ and $R^4$ is $NO_2$, then the other is $CF_3$, $CF_2CF_3$, or CN.

2. The compound of claim 1, which is selected from the group consisting of:

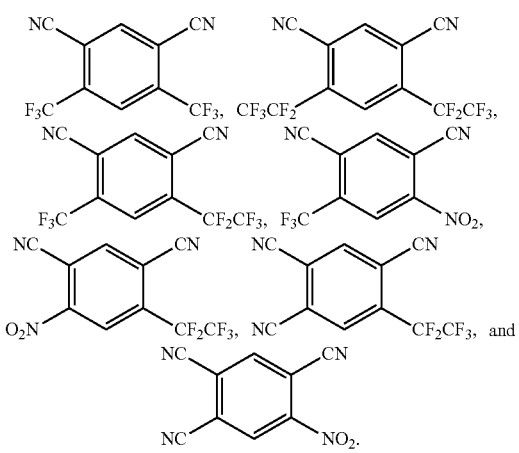

3. The compound of claim 1, which is:
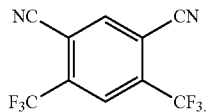
4. The compound of claim 1, which is:
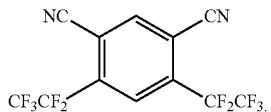
5. The compound of claim 1, which is:
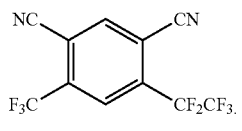
6. The compound of claim 1, which is
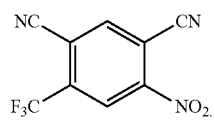
7. The compound of claim 1, which is:
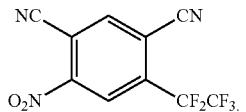
8. The compound of claim 1, which is:
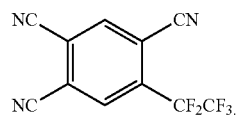
9. The compound of claim 1, which is:
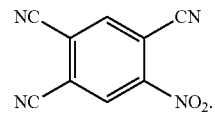
* * * * *